US00PP15912P3

(12) United States Plant Patent
Higaki

(10) Patent No.: US PP15,912 P3
(45) Date of Patent: Aug. 9, 2005

(54) ***HYDRANGEA* PLANT NAMED 'WHITE ROBE'**

(50) Latin Name: *Hydrangea macrophylla*
Varietal Denomination: White Robe

(75) Inventor: Harrison Higaki, San Mateo, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days.

(21) Appl. No.: 10/187,135

(22) Filed: Jun. 28, 2002

(65) Prior Publication Data

US 2004/0003443 P1 Jan. 1, 2004

(51) Int. Cl.[7] ..... A01H 5/00

(52) U.S. Cl. ..... Plt./250

(58) Field of Search ..... Plt./250

*Primary Examiner*—Kent Bell
*Assistant Examiner*—Louanne Krawczewicz-Myers
(74) *Attorney, Agent, or Firm*—James R. Cypher; Charles R. Cypher

(57) ABSTRACT

A new and distinct cultivar of *Hydrangea macrophylla* (Thunb.) named 'White Robe' originated as a cutting taken from the cultivar 'Buffie'. The cultivar 'White Robe' has white sepals at maturity and is distinguished from other similar cultivars of which the inventor is aware by the unique manner in which the inflorescence ages. As the mature sepals age and turn green they are highly resistant to burning and turning brown The new variety 'White Robe' further possesses the favorable characteristics of a compact growth habit and long lasting large inflorescences.

2 Drawing Sheets

Latin name of the genus and species of the plant claimed: The new plant is a variety of *Hydrangea macrophylla* (Thunb.).

Variety denomination: The new plant has been given the varietal designation 'White Robe'.

BACKGROUND OF THE INVENTION

This invention relates to a new and distinct cultivar of the Saxifragaceae family. The botanical name of the plant is *Hydrangea macrophylla* (Thunb.). The varietal denomination is 'White Robe'.

The new cultivar originated as a cutting taken from the plant *Hydrangea macrophylla* (Thunb.) 'Buffie' (unpatented). The cutting was taken on May 27, 1999. The variety 'Buffie' has pigmented sepals, and is typically grown under soil conditions with pH conditions that produce pink pigmentation. The new variety was first noticed, because it had white sepals under soil conditions that would have produced pink sepals in 'Buffie'.

'White Robe' is distinguished from other varieties of *Hydrangea* that have white sepals of which the inventor is aware by the manner it which its sepals age.

The new cultivar 'White Robe' has been successfully asexually reproduced under controlled environmental conditions at a nursery in Half Mood Bay, Calif. under the direction of the inventor over a three year period with its distinguishing characteristics remaining stable.

'White Robe' is distinguished from other white varieties of *Hydrangea* of which the inventor is aware by the manner it which its sepals age. Sepal color of 'White Robe' is predominately white at maturity. Sepals start green, and turn white as they mature. Then as the florets begin to age, the sepals turn green again. The characteristic that distinguishes 'White Robe' from all other white varieties known to the inventor is that as the mature sepals age and turn green they are highly resistant to burning and turning brown, unlike many other *Hydrangeas*. This makes the flowers of the plant more attractive for longer periods of time.

The new variety of *Hydrangea* as described herein is further characterized by its compact growth habit, and its large, long lasting inflorescences.

Asexual reproduction was first accomplished when vegetative cuttings were taken from the initially selected plant. Examination of asexually reproduced, successive generations grown in at Half Moon Bay, Calif. show that the combination of characteristics as herein disclosed for 'White Robe' remains firmly fixed.

Asexual reproduction of successive generations at Half Moon Bay was achieved by taking vegetative cuttings from selected plants five times over three years. Each new generation retained the combination of characteristics as herein disclosed for 'White Robe'.

DESCRIPTION OF THE DRAWINGS

The accompanying drawings consist of color photographs that show the typical plant form, including the inflorescence, foliage, and sepals.

The plant shown is approximately 1 years old. The plant started out as a cutting, taken from the stem of a grown plant. Two leaves were attached to the stem cutting. The cutting was placed in a 4" pot with hydrangea soil that would produce blue pigmentation in *Hydrangeas* that have pigmentation in their sepals. The cutting was placed under mist for 3 to 4 weeks until the cutting rooted. The cutting was then moved out of the misting area, but left under glass. Once the cutting produced roots, the plant was fertilized approximately twice a week. The plant was kept inside under glass for 4 to 5 more weeks and then moved outside, and fertilized once a week.

DESCRIPTION OF THE NEW PLANT

Figure 1:
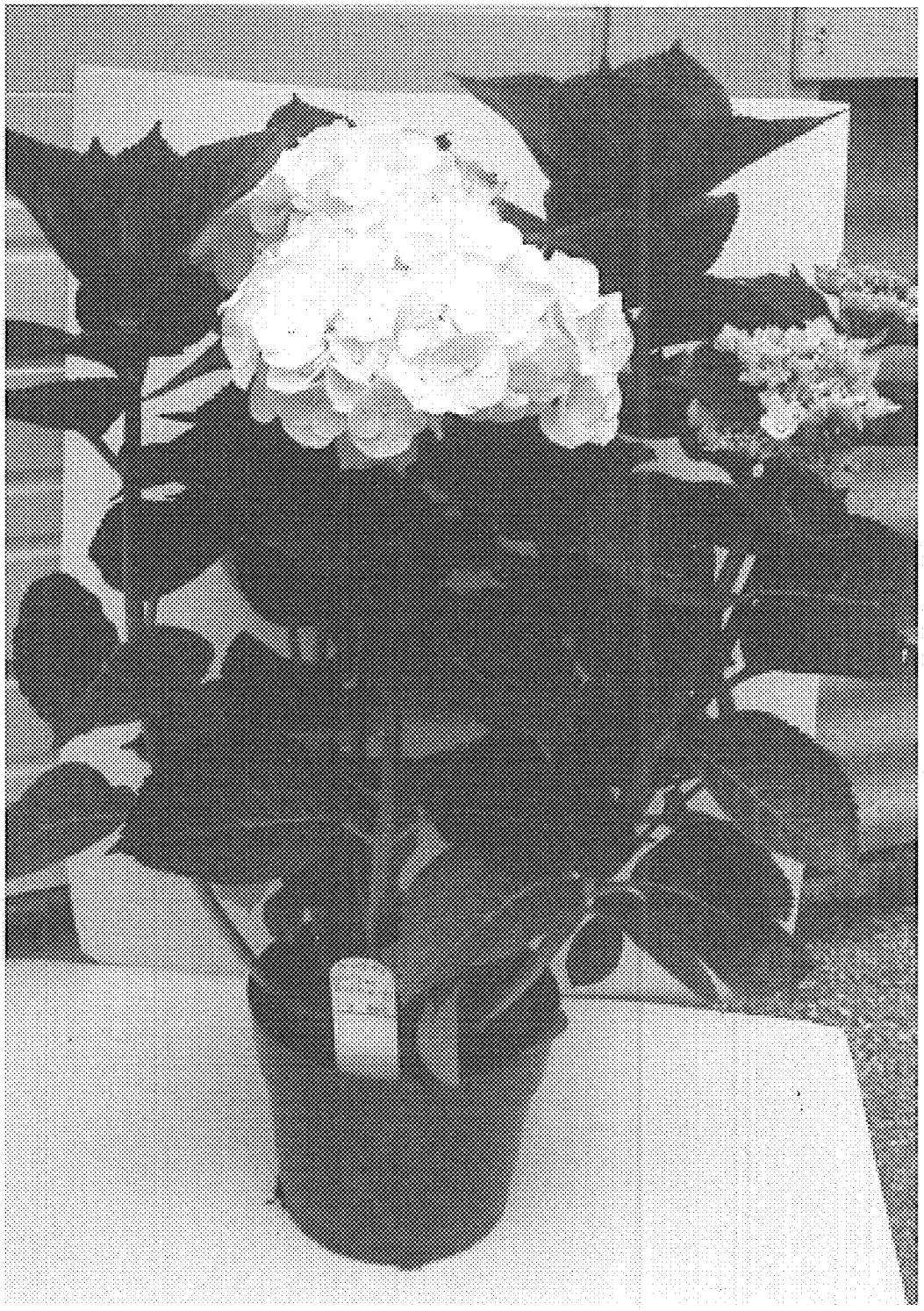
FIG. 1 is a view of the entire plant showing its form, compact growth habit, dark green foliage, inflorescence, and white sepals
Figure 2:
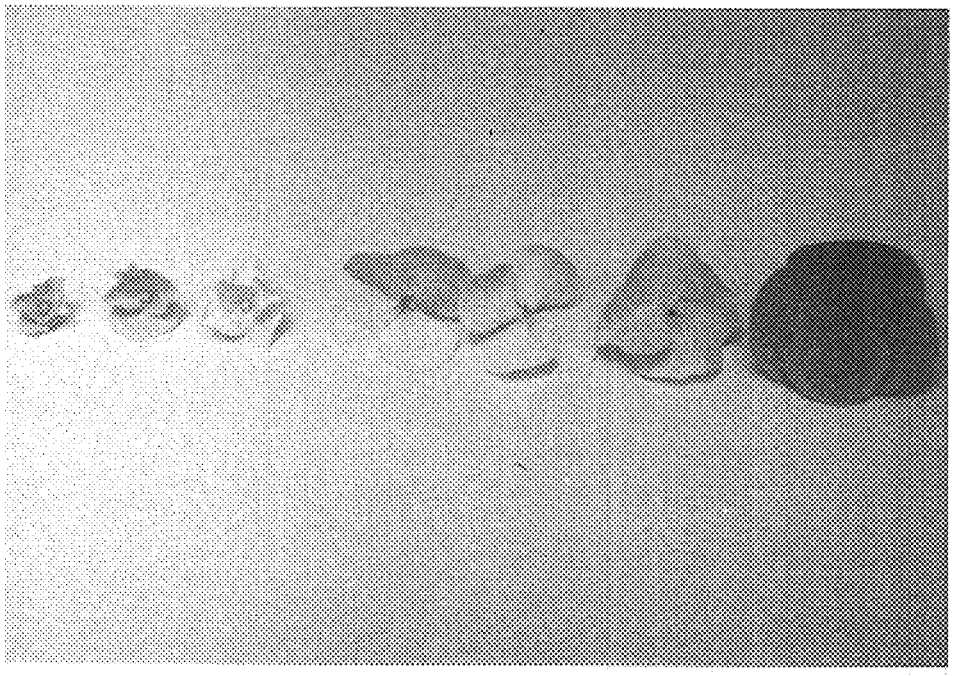
FIG. 2 is a close-up view of the individual florets illustrating the unique white sepals which, as they age, generally turn green without burning.
Figure 3:
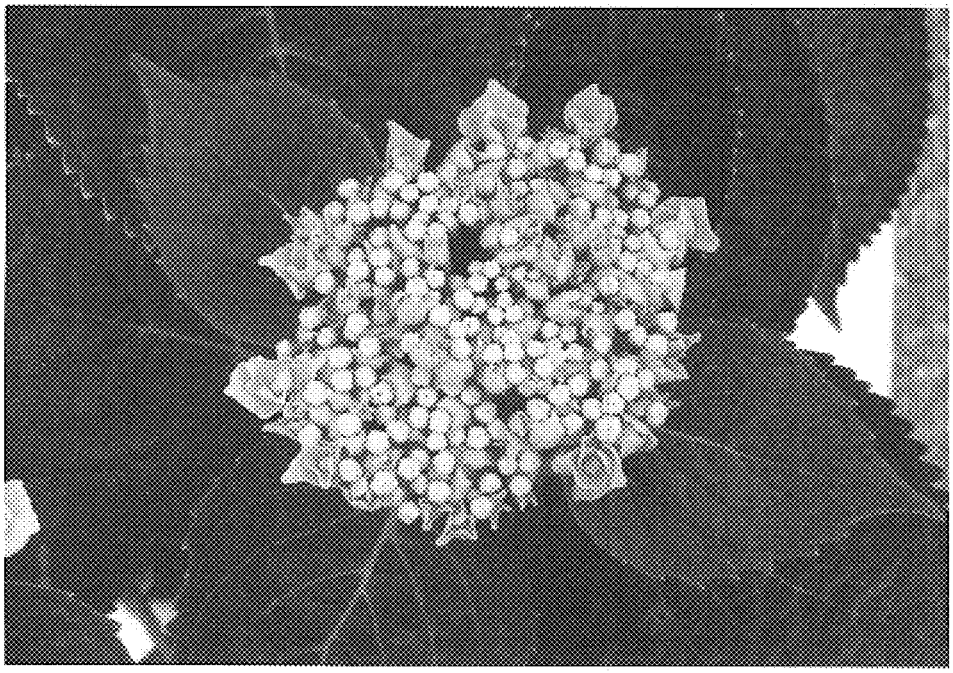
FIG. 3 is a close-up view taken from above a relatively young inflorescence of the new cultivar showing its large inflorescence.

'White Robe' has not been observed under all possible environmental conditions. The phenotype may vary significantly with variations in environment such as temperature, light intensity and day length. The following is a detailed description of a plant that started as a stem cutting and was grown in a 4" pot under the prevailing daylengths at Half Moon Bay, Calif. The plants observed were approximately 1 years old. The color determinations were made with The Royal Horticultural Society (R.H.S.) Colour Chart.

THE PLANT

Origin: Cutting.

Parent: *Hydrangea macrophylla* (Thunb.) 'Buffie'.

Classification:

*Botanic.*—*Hydrangea macrophylla* (Thunb.) 'White Robe'.

*Commercial.*—Florist *Hydrangea* 'White Robe'.

Form: Upright, compact shrub. A typical plant with a mature infloresence that is ready for sale is approximately 17" high and has a diameter of 16" when grown in a 4" pot with appropriate soil amendments.

Growth: Upright, vigorous growth habit. Inflorescence is large. The plant braches easily with shoots forming at the base of the plant. Lateral branches are similar in appearance and form to the main stems.

Stems: Lenticels are present; stems become woody as they age. The color of typical young stems and young lateral branches is R.H.S. 145 A (green group). Woody stems are R.H.S. 199 D (grey-brown group) Typical internode length on mature stems and branches is approximately 2.5".

Foliage: Abundant. Leaves are opposite on stem and lateral branches. The blades of small mature leaves are approximately 4.5" long and 3.25" wide, while large mature leaves have blades that are as long as 7.5" long and as wide as 6.5". Petioles can be as long as 1.5" to 2". There can be as many as 10 leaf pairs on a new stem below the infloresence.

*Shape of leaf.*—Elliptic with acute base and apex; margins are serrate.

*Texture.*—Glabrous; veins dominate on the underside of the leaf and are sunken on the leaf surface.

*Color.*—Mature leaves have an upper side that is R.H.S. 137 A (green group); under side is R.H.S. 147 D (yellow-green group). The veins of mature leaves are R.H.S. 145 C (yellow-green group) whether viewed from the top or the bottom of the leaf. Leaves are pinnately veined. The mid vein and veins branching off the midvein are large and prominent on the underside of the leaves.

BUDS

Form: Globose; with 4 to 5 connate petals. Buds in the very center of the inflorescence are non-sepalous. The majority of buds have sepals. They are approximately 1 mm by 1 mm. Very young floret buds are R.H.S. 145C (yellow-green group).

Aspect: Smooth.

Arrangement: Borne on branched panicles.

Color: Buds and sepals are yellow-green, and whiten as the bud matures.

INFLORESCENCE

Form: Paniculate. Terminal. 100 or more individual flowers (florets) per inflorescence. Both sepalous florets and non-sepalous florets borne on same panicle with the sepalous florets hiding the non-sepaolous florets, when the inflorescence reaches maturity. An infloresence with 100 florets may have as many as 85 sepalous florets and 15 non-sepalous florets. Plants are easily forced to bloom in June and July. Inflorescences can last on the flower as long as a year, after turning green — R.H.S. 145 A (yellow-green group). Flowers do not produce a fragrance. The peduncle or panicle for the inforescence is strong and upright, and typically 3" in length above the last leaf pair on the stem. The peduncle will bend when the plant wilts from dryness in the soil, but the peduncle can return to its upright form when the plant is watered again. Color of the peduncle is R.H.S. 145 A (green group). Pedicels for the individual florets are predominately white (R.H.S. 155D (white group)) at maturity, but turn green — R.H.S. 145A (green group) as the infloresence ages past matures. Pecidels are typically 1.5" to 3.5" long, branch at many different angles and are approximately 1 mm in diameter.

Size of inflorescence: Large. Individual inflorescence size is dependent on the number of florets. Typical inflorescences can grow as large as 10" in diameter, and 6" high.

Shape: Clusters of numerous small florets; sepalous florets are flat and overlapping one another. Sepals are persistent. Sepals elongate and greens as the inflorescence ages past maturity. Non-sepalous florets are inconspicuous and hidden by sepalous florets.

Appearance: Showy.

FLORETS

General: Sepalous florets are perfect and complete, although petals, stamens and ovary generally fall off as floret approaches maturity.

Corrola: Generally there are 5 petals with 1 petal being wider than the other 4. In the sepalous florets the petals generally fall off before the inflorescence reaches maturity.

Reproductive organs:

*Stamens.*—8 to 10 stamens. Pollen is white — R.H.S. 155D (white group). Plant produces abundant pollen. Filament is purple-blue and approximately 2 mm long, but color depends on pH of the soil. Anther is 1 mm long and is purple-blue (again color depends on pH of the soil) when young and begins to green as floret approaches maturity. Anther is regular and basally attached.

*Stigma.*—Two to three-pronged stigma on one pistil per floret. Stigma is purple-blue, depending on the pH of the soil, and barely protrudes from the ovary.

*Ovary.*—Green in color — R.H.S. 145 A (yellow-green group); single ovary that is partially inferior.

Sepalous florets:

*Number of sepals.*—4 or 5 sepals per floret, usually 4.

*Aspect of sepals.*—Smooth.

*Shape of sepals.*—Reniform with acuminate apex. Edges often wavy when the floret is young.

*Size of sepals.*—Usually 1 dominant sepal, 2 smaller but equally-sized sepals, and 1 small sepal. Largest sepal, when sepals are their whitest is typically 3 cm long and 4 mm wide, the medium sized sepals are typically 2.8 cm long by 3.2 mm wide, and the smallest sepals are typically 2.5 cm long and 3 cm wide.

*Coloration of sepals.*—Predominately white (R.H.S. 155D (white group)) at maturity on both the upper surface and the lower surface. As inflorescence ages past maturity sepals turn green (R.H.S. 145 A (yellow-green group)) on both the upper surfaces and the lower surfaces, generally without burning or turning brown.

Fruit: Brown and dry.

Seeds: Brown.

Disease/pest resistance: The plant has not shown any particular susceptibility or strong resistance to common plant diseases and pests for this cultivar.

I claim:

1. A new and distinct *Hydrangea macrophylla* plant named 'White Robe' substantially as herein shown and described.

* * * * *